United States Patent [19]
Acevedo et al.

[11] Patent Number: 5,459,243
[45] Date of Patent: Oct. 17, 1995

[54] APPARATUS AND PROCESSES FOR THE LARGE SCALE GENERATION AND TRANSFER OF DIAZOMETHANE

[75] Inventors: Oscar Acevedo, San Diego; Bruce Ross, Carlsbad; Robert S. Andrews, San Juan Capistrano; Robert Springer; Phillip D. Cook, both of Carlsbad, all of Calif.

[73] Assignee: Isis Pharmaceuticals, Inc., Carlsbad, Calif.

[21] Appl. No.: 209,154

[22] Filed: Mar. 10, 1994

[51] Int. Cl.$^6$ ....................... C07C 245/12; C07C 245/16
[52] U.S. Cl. ............................................ 534/565; 534/558
[58] Field of Search ............................................. 534/565

[56] References Cited

U.S. PATENT DOCUMENTS 4,197,410  4/1980  Sekiya et al. ............................ 560/159

FOREIGN PATENT DOCUMENTS 63-51366  3/1988  Japan ...................................... 534/565

OTHER PUBLICATIONS

Blencowe et al. Antisense Probing of the Human U4/U6 snRNP with Biotinylated 2'-OMe RNA Olignucleotides *Cell* 1989 59:531–539.
Chavis et al. Synthesis of 2',3'-Differentiated Ribonucleosides via Glycosylation Reactions with 2-O-Me or 2-OTBDMS Ribofuranose Derivatives *J. Org. Chem.* 1982 47:202–206.
Inoue H et al., Synthesis and Properties of Novel Nucleic Acid Probes *Nucleic Acids Research* 1985 16:165.
Lamond et al. Probing the Structure and Function of U2 snRNP with Antisense Oligonucleotides Made of 2'-OMe RNA *Cell* 1989 58:383–390.
Sproat et al. Highly effecient chemical synthesis of 2'-O-methyloligoribonucleoties and tetrabiotinylated derivatives *Nucleic Acids Research* 1989 17:3373.
Wagner et al. Antisense Gene Inhibition by Oligonucleotides Containing C-5 Propyne Pyrimidines *Science* 1993 260:15510.
Wagner et al. A simple procedure for the preparation of protected 2'-O-methyl or 2'-O-ethyl ribonucleoside-3'-O-phosphoramidites *Nucleic Acids Research* 1991 19:5965–5971.
Black, *Aldrichimica Acta*, 16(1), 1983, 3–10.
Bush et al., *Anal. Biochem.*, 106, 1980, 351–362.
Cohen, *J. Chromat.*, 303, 1984, 193–196.
de Boer, Organic Syntheses, Collective vol. IV, Rabjohn, N., Ed., New York, John Wiley & Sons, 1963, 250–253.
Ghazi, *Synth. Comm.*, 22(19), 1992, 2853–2857.
Hudlicky, *J. Org. Chem.*, 45, 1980, 5377–5378.
Kikuda et al., *Chemical Abstracts*, 91:18436 (1978).
Kikuda et al, *Ehime Kenritsu Eisel Kenkyusho Nempo*, 39, 1977, 43–47.
Ngan et al., *J. Chromatogr. Sci.*, 29(1), 1991, 8–10.
Schlenk et al., *Anal. Chem.*, 32(1), 1960, 1412–1414.
Stempel et al., *Methods Enzymol.*, 126 (Biomembranes, Pt. N), 1986, 618–639.
Walker et al., *J. Chromatogr.*, 241, 1982, 390–391.
Patent Abstracts of Japan, Abstract of JP 63–51366, Mar. 4, 1988.
Martin et al, *Biochemistry*, 7, 1968, 1406–1412.
Robins et al., *J. Org. Chem.*, 39(13), 1974, 1891–1899.

*Primary Examiner*—Robert W. Ramsuer
*Assistant Examiner*—Fiona T. Powers
*Attorney, Agent, or Firm*—Woodcock Washburn Kurtz Mackiewicz & Norris

[57] ABSTRACT

For large scale preparation of pyrimidine ribonucleosides, the intermediate 2-O-methyl-(or ethyl)-1,3,5-tri-O-benzoyl-α-D-ribose can be prepared using a diazomethane (or diazoethane) reaction that is controlled via an inert solvent transferring system. This transfer system allows for large scale preparations of the pyrimidine ribonucleosides.

4 Claims, 1 Drawing Sheet

APPARATUS AND PROCESSES FOR THE LARGE SCALE GENERATION AND TRANSFER OF DIAZOMETHANE

FIELD OF THE INVENTION

This invention is directed to an apparatus and improved processes for the large scale generation and transfer of diazomethane and related diazo lower alkanes. The invention further relates to the synthesis of ribose sugars, such as 2-O-methyl-1,3,5 -tri-O-benzoyl-α-ribose, and to pyrimidine nucleosides prepared from this sugar. The invention includes the use of diazomethane as an alkylating agent.

BACKGROUND OF THE INVENTION

Unmodified natural phosphodiester oligonucleotides are cleaved by nucleases. Nuclease cleavage of these unmodified phosphodiester oligodeoxynucleotides is reported in serum and by introduction in other biological systems. Certain modifications to oligonucleotides have resulted in resistance to nucleases. One such modification that yields increased nuclease stability is the incorporation of methyl groups on the 2' position in an oligonucleotide. These nucleotides are prepared from the corresponding nucleosides and are usually introduced into the oligonucleotide using phosphoramidate intermediates. The usefulness of such 2'-O-modified oligonucleotides is such that certain 2'-O-nucleotide phosphoramidates are now commercially available from several sources both as the amidite and as the derivatized solid supports. These reagents are used to make oligonucleotides that in turn are used as diagnostic reagents, as research reagents and for other uses.

2'-O-Methyl ethers of ribonucleosides are natural modifications that are found in vivo as a minor component of many types of RNA. It has been shown that 2'-O-alkyl oligonucleotides are resistant to degradation by either DNA or RNA specific nucleases (Sproat, et. al., *Nucleic Acids Res.*, 1989, 17, 3373), and form hybrids of high thermal stability with complementary RNA. Wagner., et. al., *Nucleic Acids Research.*, 1991, 19, 5965–5971. These hybrids are useful as research reagents such as probes. Such probes allow for determining the functions of nucleic acids transcription factors and other related cellular entities. Such utility is illustrated in a number of publications as for example, Lamond, et. al., *Cell*, 1989, 58, 383–390 or Blencowe, et. al., cell, 1989, 59, 531–539 . As stated by Wagner, "2'-Methyloligoribo-nucleotides are oligonucleotide analogs which exhibit high resistance to both DNA and RNA specific nucleases and form hybrids of high thermal stability with complementary RNA." These analogs, as well as the recently described 2'-O-allyl oligoribonucleotides have proven to be valuable antisense compounds for studying snRNP-mediated pre-mRNA splicing and processing. Sequence-specific inhibition of histone pre-mRNA processing in vitro has been demonstrated using 2'-methyl or 2'O-ethyl oligoribonucleotide 19 mers complementary to the 5'-end of the U7-snRNP-RNA. These compounds were said to inhibit processing at a 300-fold lower concentration than that required using the corresponding DNA oligomer.

Synthesis of 2'-O-methyl oligoribonucleotides was first reported in 1985 using phosphodiester chemistry. Inoue, et. al., *Nucleic Acids Res. Symposium Series* 1985, 16, 165. Early methods of synthesizing 2'-O-methyl pyrimidine ribonucloesides generally started with the ribonucleoside. The ribonucleoside is protected at the primary 5'-hydroxyl. If necessary, the primary amino function of the aglycon was also protected. This is followed by a nonselective substitution of the 2'- and 3'-hydroxyls. This latter operation necessitates separation of the isomeric mixture by chromatography or fractional crystallization. Lengthy separations and low overall yields are a common limitation with this method of synthesis.

More recent methods of synthesizing 2'-O-methyl-pyrimidine ribonucleosides involve alkylation of 2'-O-methyl-1,3,5 tri-O-benzoyl-e-D-ribose using diazomethane. The sugar used in the alkylation step is 1,3,5-tri-O-benzoyl-α-D-ribose. $BF_3$ is conventionally used as a Lewis acid catalyst for this reaction. It has further been reported by C. Chavis,. st. al., *J. Org. Chem.*, 1982, 47, 202–206, that $BF_3$ etherate also prevent acyl migration during the synthesis. The product is purified by chromatography to give about a 75% yield. However, only small scale reactions (up to 5 g the product sugar) have been reported for this synthesis due to the hazards of using diazomethane which is an acutely toxic and explosive reagent.

There is a growing demand for large quantities of 2-O-methyl-1,3,5 -O-benzoyl-α-D-ribose for use as a primary intermediate to synthesizing 2'-O-methyl-pyrimidine ribonucleosides. There is a further demand for large quantities of 2'-O-methyl-pyrimidine ribonucleosides for use in preparing oligonucleotides. There is a similar demand for large scale production of diazomethane, diazoethane and diazopropane.

It is an object of this invention to provide apparatus for a large scale, controlled generation of diazomethane, diazoethane and diazopropane.

It is a further object of this invention to provide improved processes for preparing 2-O-methyl-1,3,5-tri-O-benzoyl-α-D-ribose via a large scale diazomethane reaction along with the corresponding 2'-O-ethyl and 2'-O-propyl counterparts.

SUMMARY OF THE INVENTION

In accordance with this invention there is provided apparatus for the large scale production of diazomethane, diazoethane or diazopropane. Hereinafter the three materials may be referred to as "diazo lower alkanes." The apparatus includes a reaction vessel for the generation of diazomethane diazoethane or diazopropane through contact of a nitroso precursor compound with an aqueous base in the presence of an organic solvent compatible with diazo lower alkanes. The apparatus further includes vessels for drying the organic solution of diazomethane diazoethane or diazopropane. A basic drying agent compatible with the diazomethane or diazoethane and the solvent in maintained in the drying vessels. The apparatus further includes a vessel for storing the dry solution of diazomethane diazoethane or diazopropane while maintaining it within an inert, gaseous environment. Further included in the apparatus is a gas source in communication with the vessels for effecting a dry, chemically inert gaseous environment. The apparatus also includes the use of gas pressure and/or partial vacuum for selectively increasing or decreasing the head space pressure in each of the vessels to effect safe transfer. Included in the apparatus is inert tubing in communication with each vessel for transferring the diazomethane diazoethane or diazopropane solution from a drying vessel to the next drying vessel and from the last drying vessel to the storage vessel while maintaining a dry, inert gaseous environment. Inert tubing in communication with the storage vessel is also provided for delivering the organic solvent containing the diazo lower alkane solution from the storage vessel also while maintaining the inert gaseous environment.

In a preferred embodiment of the invention the apparatus is composed essentially of a polymer inert to diazomethane or diazoethane. Such a preferred polymer is a polymerized, fluorinated hydrocarbon, such as a Teflon® species.

In the practice of the invention it is preferred to maintain each of the reaction, drying and storage vessels at a temperature below room temperature. A more preferred temperature is from about 0° C. to about 15° C. It is further preferred to effect all solution transfers through tubing in communication with the interior of the vessels. Additionally it is preferred to use a noble gas for maintaining a dry, chemically inert gaseous environment in the drying and storage vessels. It is also preferred to use the application of partial vacuum or of noble gas pressure to effect all transfers of the diazomethane, diazoethane or diazopropane solution between vessels.

In the practice of the invention it is preferred to use an alkali metal hydroxide as the basic drying agent. In a further preferred practice of the invention an alkylation chamber is utilized wherein the delivery of the diazomethane or diazoethane solution to a reactant species to be alkylated is effected.

It is preferred to use chlorinated aliphatic solvents, especially methylene chloride as the organic solvent. It is preferred that transfer of the diazomethane, diazoethane or diazopropane solution be adjusted to achieve transfer of from about 1% to about 5% by volume of the diazo lower alkane solution per minute from one vessel to the next. The transfer rate is adjusted by application of partial vacuum or of noble gas pressure. In a preferred application of the invention the transferring is adjusted to achieve transfer of from about 1.5 to about 3% by volume of the solution per minute.

The methods for the large scale production of a nucleoside 2'-O-methyl or -O-ethyl ether is facilitated by contacting the corresponding 2'-O-hydroxy compound with diazomethane, diazoethane or diazopropane delivered from the storage vessel into the reaction chamber.

The present invention provides improved processes for the large scale production of diazomethane, diazoethane or diazopropane. These processes include generating diazomethane, diazoethane or diazopropane through contact of a nitroso precursor compound with an aqueous base in the presence of an organic solvent for diazomethane or diazoethane. The process further includes drying the solution of organic solvent and the diazomethane or diazoethane a plurality of times with a basic drying agent compatible with diazomethane or diazoethane and the solvent and storing the dry solution of diazomethane or diazoethane in the solvent in a storage vessel. The process further includes maintaining a dry, chemically inert gaseous environment in the vessels for drying and storage and delivering the organic solvent containing the diazomethane or diazoethane from the storage vessel while maintaining the inert gaseous environment.

In a preferred embodiment of the invention the organic solvent has a density greater than the aqueous base. In a further preferred embodiment of the invention the temperature of the diazomethane or diazoethane solution is maintained from about 0° C. to about 15° C.

In a preferred embodiment of the invention the drying and storing steps of the organic solvent containing the diazomethane or diazoethane is effected in separate vessels and the organic solvent containing the diazomethane or diazoethane is transferred between the separate vessels using a differential in pressure.

DETAILED DESCRIPTION OF THE INVENTION

Figure 1:
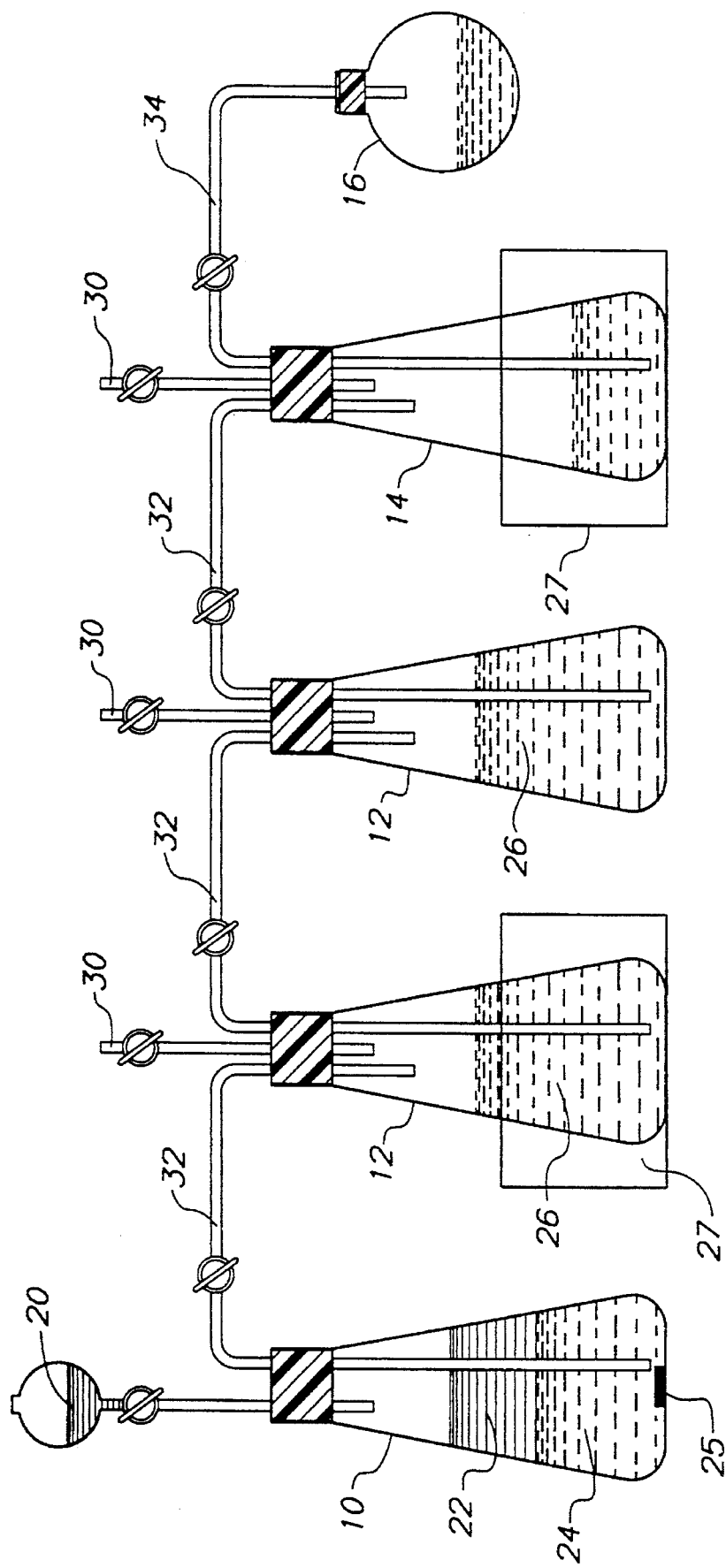
FIG. 1 is an elevational view of a preferred apparatus used in the processes of this invention.

2-O-Methyl-1,3,5-tri-O-benzoyl-α-D-ribose is a key intermediate for use in the synthesis of 2'-O-methyl pyrimidine ribonucloesides. 2'-O-Methyl pyrimidine ribonucleosides, in turn are utilized in the synthesis of novel oligonucleotides which are useful as research probes and primers, especially for the study of enzyme biochemistry and protein-nucleic acid interactions and gene expression and for other uses as well. Corresponding 2'-O-ethyl and 2'-O-propyl analogs are expected to be similarly useful.

One approach to large scale synthesis of 2'-O-methyl-pyrimidine ribonucleosides is to alkylate the sugar prior to glycosylation using diazomethane. However, diazomethane is carcinogenic, mutagenic, teratogenic, toxic, and explosive. To work with large amounts of this material, a method of transferring the diazomethane solution that eliminates the need to manually move the solution from vessel to vessel is highly desirable.

The processes of the invention allow for elimination of manually transfer of diazo lower alkane solutions. The diazo lower alkane solution is transferred from one vessel to the next using an inert transfer tubing system. The equipment required to run this reaction can be set up at the beginning of the synthesis. Once the synthesis is started, all manipulations of solutions can be controlled by vacuum or gas pressure, via inert, two way valves and inert tubing. The generation vessel and all other vessels used in this syntheses are preferably made of an inert material which can include glass only if the surfaces are not scratched. Ground glass is never used because diazomethane gas condensing on ground glass has been reported to be explosive.

One preferred setup involves thoroughly cleaning and drying all vessels, stir bars, and transfer tubing. Stir plates, ice baths and vessels are set up as per the drawings. Rubber or other inert stoppers are placed on the vessels and the addition funnel and all transfer tubing is inserted. All vessels and tubing apparatus are clamped securely into place. Ice baths are charged with ice and water to precool all vessels. Stir bars are put into the generation and reaction vessels. Drying agent is put into the drying vessels. For safety, protective barriers are placed in front of all vessels and reagents are added by reaching behind protective barriers. Once the reagents are added to the generation vessel and the reaction vessel, the remainder of all transfers and additions are made by opening and closing valves while applying either vacuum or inert gas pressure.

The procedure for diazomethane is analogous to that for diazoethane and diazopropane. 1-Methyl-3-nitro-1-nitrosoguanidine (MNNG), is added to a rapidly stirred biphasic mixture of aqueous base and $CH_2Cl_2$. MNNG reacts with the aqueous base to yield diazomethane which is solubilized in the $CH_2Cl_2$. The $CH_2Cl_2$/diazomethane is transferred to a drying vessel and dried over a drying agent. The drying agent is preferably basic such as aklali metal hydroxide, especially KOH. A plurality of drying stages is employed in accordance with preferred embodiments. The dry solution is then transferred to a storage vessel. The $CH_2Cl_2$/diazomethane can be subsequently metered into a reaction vessel such as one which contains 1,3,5-tri-O-benzoyl-α-D-ribose and boron trifluoride etherate in $CH_2Cl_2$. Work up and purification yields for example 2-O-methyl-1,3,5-tri-O-benzoyl-α-D-ribose.

The process as set forth in this specification enables the reaction of large amounts of (MNNG) e.g. 100 g, or greater. However, reactions of smaller scale can also be conducted in the same manner. MNNG is available as a stable crystalline compound which generates diazomethane upon treatment with aqueous alkali. Another reagent that is routinely used for generating diazomethane is Diazald™, N-methyl-N-nitroso-p-toluene-sulfonamide available from Aldrich.

When reacting (MNNG) on a scale of about 100 g the reagent is preferably added at about 1–3 g/min. This addition rate can be increased for larger scales. The addition of MNNG to the rapidly stirred biphasic solution causes a reaction, generating diazomethane gas. Too fast of an addition will create a layer of diazomethane gas above the reaction solution which is extremely volatile and can explode. The maximum rate of addition is determined by the ability of the organic solvent to dissolve the diazomethane that is generated. Diazomethane gas may detonate if it is allowed to escape from the generation vessel. To facilitate the solution, an aqueous, strongly basic solution and an organic solution are rapidly stirred. The generation vessel is preferably kept in an ice bath and the temperature of the biphasic mixture maintained at or below 15° C. The temperature of this mixture will also be a controlling factor in the rate of addition. It is necessary to slow the rate of addition if the temperature of the reaction exceeds 15° C.

The biphasic solution is conveniently made up of about one part aqueous base and about 2 parts organic solvent. Preferably KOH is used as the base however other bases may also be used. The concentration of the aqueous base needs to be sufficiently high for rapid generation of diazomethane. In the illustrative examples, 40% KOH was used, however other concentrations can also be used. If the concentration of the base is too low it will diminish the ability of the biphasic mixture to react with the MNNG and slow down the reaction process. In the illustrative examples below $CH_2Cl_2$ is used as the organic part of the mixture but any inert organic solvent that dissolves diazomethane and has a freezing point below about 0° C. can be used. It should be noted that diazomethane is reported to decompose slowly in ether and dioxane at low temperatures and that sharp edges formed in the solvent, such as crystals from freezing, can cause an explosion.

The diazomethane/$CH_2Cl_2$ phase of this mixture is transferred to a drying vessel containing KOH, NaOH, or other suitable drying agent which is maintained in an ice bath. Alternative drying agents may be used. Alkali metals, as opposed to their hydroxides, are not preferred as they are reported to produce explosions. The transfer is facilitated utilizing the transfer system described in detail below. This enables large amounts of diazomethane solution to be transferred without handling the reaction flasks. The solution of diazomethane is dried for at least 10 minutes and transferred to at least one further drying vessel. The solution is then transferred to a storage vessel which is cooled in an ice bath.

Reactants such as 1,3,5-tri-O-benzoyl-α-D-ribofuranose is dissolved in $CH_2Cl_2$ and cooled to between 0° C. and 15° C. using an ice bath in an alkylation vessel. Boron trifluoride etherate is added to the cooled solution and the solution rapidly stirred. About eight equivalents of MNNG are used for each equivalent of 1,3,5-tri-O-benzoyl-α-D-ribofuranose. The boron trifluoride etherate is used catalytically at a level of about 0.06 equivalents to prevent acyl migration. The volume of solvent in the reaction vessel is a little over one third of the solution being added.

The diazomethane/$CH_2Cl_2$ is metered out of the holding vessel into the reaction vessel. The metered rate of the addition is maintained at a preferred level from about 1.5% to about 3.0% of the total volume of the dried diazomethane solution per minute. For a typical 800 ml/125 g MNNG scale synthesis the metered rate is about 15 ml per minute. This can be accomplished by adjusting the flow rate with gas pressure applied on the top of the holding flask and as a secondary means by adjusting the two way inert valve in line to the reaction vessel. The rate of addition of the diazomethane/$CH_2Cl_2$ into the reaction vessel is of prime importance to the reaction yield. When the rate of addition is too fast or if the stirring is discontinued during addition the resulting exotherm can trigger an explosion. If the addition is too slow, the diazomethane may polymerize. Further, a large amount of polymethylene may be formed reducing the yield. Temperature, addition rate, and stir rate are closely monitored throughout the addition.

The mixture is stirred for about 30 minutes after the addition is completed. Conventional workup and purification gives the product. A typical yield is about 70%. As illustrated in the examples, a 125 g MNNG reaction gives about 36.6 g of pure 1,3,5-tri-O-benzoyl-2-O-methyl-α-D-ribofuranose.

The above process has been used to synthesize hundred gram quantities of the 1,3,5-tri-O-benzoyl-2-O-methyl-α-D-ribofuranose compound. Preferred apparatus is described in detail below.

All tubing, vessels, and valves are made of inert material. Ground glass or glass having scratched surfaces that will be in contact with diazomethane solution are not used due to hazard of explosion. Materials include but are not limited to teflon, glass and polyethylene. The preferred material is teflon because of the availability of teflon tubing, piping and corresponding valves. All the necessary components are available from a number of distributors e.g. U.S. Plastics Inc. Valves are two way large orifice type preferably Hamilton inert two way plug valves (Z12,442-7, Aldrich), or teflon 2 way valves U.S. Plastics Inc.

The following description of a preferred apparatus refers to FIG. 1. The nitroso precursor is added to a reaction vessel, 10 such as through an addition funnel, 20. A biphasic mixture of aqueous base, 22 and organic solvent, 24 is rapidly stirred such as by stir bar, 25 and a magnetic stir plate. Transfer of the organic diazomethane, diazoethane or diazopropane layer is facilitated through the transfer tube, 32. A reduced pressure can be effected through the pressure/vacuum tubing, 30 thereby causing the organic phase of the reaction vessel to be transferred. Drying agent, 26 contacts the organic phase and the transfer process is repeated in a second drying vessel, 12. All the vessels are isolated from each other by valves as are the gas pressure/vacuum tubes. The valves are closed until specifically needed to allow a transfer of solution or increase or decrease of gas pressure in a vessel. The vessels are cooled in an ice baths, 27. The organic solution is transfered from the second drying vessel, 12 to the storage vessel 14 and is metered from the storage vessel to the alkylation vessel, 16 through transfer the transfer tubing, 34. Representative 2-substituted pyrimidines that can be prepared using the processes of this invention include: 2-(aceton-1-yl)-1-(3,5-di-O-benzoyl-2-O-methyl-β-D-ribofuranosyl)pyrimidin-4-one. A representative unsubstituted pyrimidine that is prepared using the process of this invention is: 2'-O-methyluridine.

Representative 4-substituted pyrimidines that are prepared using the process of this invention include: 4-chloro-1-(3,5-di-O-Benzoyl-2 methyl-β-D-ribofuranosyl)pyrimidin-2-one, 4-(2-hydroxy-1-hexen-1-yl)-1-(3,5-di-O-benzoyl-2-O-methyl-β-D-ribofuranosyl)pyrimidin-2-one, 4-(2,5-dihydroxy-1-hexen-1-yl)-1-(3,5 -di-O-benzoyl-2-O-methyl-β-D-ribofuranosyl)pyrimidine-2-one.

Representative 5-Substituted pyrimidines that are prepared using the process of this invention include: 2'-O-methyl-5-cyanouridine; 2'-O-methyl-5-methyluridine; 2'-O-methyl-5-fluorouridine; 2'-O-methyl-5-nitrouridine; 2'-O-methyl-5-(1-propynyl)-uridine; 2'-O-methyl-5-trifluorouridine; N-4-benzoyl-2'-O-methyl-5-methylcytidine.

Example 1

2-O-Methyl-1,3,5-tri-O-benzoyl-α-D-ribose.

1-Methyl-3-nitro-1-nitrosoguanidine (125 g, 0.85 moles) was added in small portions to a rapidly stirred biphasic solution of 40% potassium hydroxide (400 ml) and methylene chloride (800 ml) over a period of 60 minutes. The temperature of the mixture was maintained at or below 4° C. The $CH_2Cl_2$ layer was transferred to an erlenmeyer flask containing 20 g of potassium pellets. The transfer was achieved utilizing the teflon transfer apparatus of FIG. 1. This organic solution was kept at 4° C. for 15 minutes. The above drying procedure was repeated utilizing the teflon transfer apparatus and kept at 4° C. for 10 minutes. The organic solution was then transferred via teflon transfer apparatus to an addition flask and kept at 4° C. The organic solution was then added by metering through a controlled teflon transfer/metering system into a cold rapidly stirred solution of 1,3,5-tri-O-benzoyl-α-D-ribofuranose (Pfanshtiehl, 50 g, 0.11 moles) and boron trifluoride etherate (0.8 ml, 0.007 moles) in $CH_2Cl_2$ (300 ml) using a teflon transfer apparatus regulated by argon gas pressure. Both flasks are kept at 4° C. during the addition.

The erlenmeyer reaction flask was kept in an ice bath for 30 minutes after the addition of the diazomethane solution and then filtered using suction. The clear yellow filtrate was washed with cold, saturated sodium bicarbonate (3×200 ml), dried over sodium sulfate, filtered and evaporated to yield 53 g of a light yellow syrup, $R_f$=0.80, chloroform/acetone 19:1. This syrup was flash-chromatographed on a silica gel column (500 g) using methylene chloride (2l) and then $CH_2Cl_2$/acetone (98: 2, 2l) to afford 36.6 g (71%) of clear syrup. $^1$H NMR ($CDCl_3$): δ3.46 (s, 3H, $OCH_3$), 4.21 (dd, $J_{2,3}$=6.3 Hz, 1H, H-2), 4.65 (m, 2H, H-5, 5'), 4.80 (m, 1H, H-4), 5.71 (dd, $J_{3,4}$=2.3 Hz, 1H, H-3), 6.76 (d, $J_{1,2}$=4.3 Hz, 1H, H-1), 7.20–8.30 (m, 15H, aromatic).

EXAMPLE 2

General Method for Glycosylation
Preparation of 3',5'-di-O-benzoyl-2'-O-methyl-5-trifluoromethyluridine.

5-Trifluoromethyluracil (7.6 g, 42 mmoles) and ammonium sulfate (0.1 g) were suspended in hexamethyldisilazane (40 ml). The mixture was heated to reflux under an argon atmosphere for 16 hours. The resulting solution was concentrated (50° C., 1 mm) to a colorless, clear oil. While maintaining the inert atmosphere, the oil was dissolved in dry acetonitrile (100 ml) and transferred via cannula to a reaction vessel containing 2-O-methyl-1,3,5 -tri-O-benzoyl-α-D-ribose (20.0 g, 42 mmoles). The stirred solution was treated with trimethylsilyl trifluoromethanesulfonate (7.2 ml, 37 mmoles) in one portion at room temperature. The reaction was monitored by tlc, if the reaction was not complete after 30 minutes, an additional 0.2 equivalents of catalyst is added. After 30 minutes, the reaction was diluted with $CH_2Cl_2$ (200 ml) and washed with saturated aqueous sodium bicarbonate (100 ml). The aqueous layer was back-extracted with $CH_2Cl_2$ (m). The organic layers were combined, dried (sodium sulfate), filtered and concentrated under reduced pressure to afford 23.0 g of offwhite foam as a 9:1 β/α anomeric mixture of products based on the H-1' resonances (αat 6.43 ppm). The pure β product crystallized from methanol (100 ml) to give 13.9 g (62%), white crystals, mp 156°–158° C. 1H NMR (DMSO-$d_6$):δ3.38 (s, 3H, $OCH_3$), 4.5–4.7 (m, 4H, H-2',4',5'), 5.63 (m, 1H, H-3'), 5.92 (d, J=3.9 Hz, 1H, H-1'), 7.5–8.1 (m, 10 H, Bz), 8.35 (s, 1H, H-6) and 12.05 (br s, 1H, NH). Anal. Calcd for $C_{25}H_{21}F_3N_2O_8$ (466.44): C, 56.28; H, 3.93; N, 5.24. Found: C, 56.42; H, 3.93; N, 5.19.

EXAMPLE 3

2'-O-Methyl-5-trifluoromethyluridine.

3',5'-Di-O-benzoyl-2'-O-methyl-5-trifluoromethyluridine (10.6 g, 20 mmoles) was dissolved in dry methanol (250 ml). Sodium metal (0.7 g, 30 mmoles) was added and the resulting solution was stirred at room temperature for 17 hours. Ammonium chloride (1.6 g, 31 mmoles) was added and the solvent was removed under reduced pressure. The residue was chromatographed on a silica gel (100 g) column eluting with a gradient of 0 to 10% methanol in $CH_2Cl_2$ to afford 6.1 g (94%) 2' -O-methyl-5-trifluoromethyluridine as a white solid, mp 192°–194°. $^1$H NMR (DMSO-$d_6$): δ3.43 (s, 3H, $OCH_3$), 3.5–3.8 (m, 2H, H-5'), 3.8–4.0 (m, 2H, H-3',4'), 4.12 (m, 1H, H-2'), 5.18 (d, J=7 Hz, 1H, 3'-OH), 5.40 (br t, 1H, 5'-OH), 5.78 (d, J=2.5 Hz, 1H-1'), 8.92 (s, 1H, H-6), 11.80 (br s, 1H, N-H). Anal. Calcd for $C_{11}H_{13}F_3N_2O_6$ (326.23): C, 40.49; H, 3.99; N, 8.59. Found: C, 40.42; H, 4.17; N, 8.32.

EXAMPLE 4

2'-O-Methyl-5-cyanouridine.

3',5'-Di-O-benzoyl-2'-O-methyl-5-trifluoromethyluridine (1.0 g, 2.1 mmoles) was dissolved in concentrated ammonium hydroxide (60 ml) and heated in a sealed tube at 55° C. for 16 hours. The solvent was removed under reduced pressure and the residue was chromatographed on silica gel (30 g) using a gradient of 0–5% methanol in $CH_2Cl_2$ to give 0.3 g (50% crude yield) of oil. A small portion of 2'-O-Methyl-5-cyanouridine crystallized from methanol as a slightly impure white solid, mp 208°–211° C. IR (potassium bromide pellet) 2240 $cm^{-1}$ (sharp, CN); $^1$H NMR (DMSO-$d_6$): δ3.45(s, 3H, $OCH_3$), 3.5–3.6 (m, 1H, H-5'), 3.7–3.9 (m, 3H, H-3',4',5'), 4.13 (m, 1H, H-2'), 5.17 (d, J=6 Hz, 1H, 3'—OH), 5.48 (br t, 1H, 5'—OH), 5.75 (br s, 1H, H1'), 8.99 (d, J=1.5 Hz, 1H, H-6), 12.08 (br s, 1H, N—H). Anal. Calcd for $C_{11}H_{13}N_3O_6$ (283.24): C, 46.64; H, 4.63; N, 14.83. Found: C, 45.98; H, 4.63; N, 14.35.

EXAMPLE 5

3',5'-Di-O-benzoyl-2'-O-methyluridine.

Uracil (1.1 g, 9.7 mmoles) was glycosylated as described in the General Method of Example 2 to afford 5.1 g of off-white foam as a 13:1 β/α anomeric mixture of the dibenzoyl intermediate based on the H-1') resonances (α at 6.36 ppm). The pure β product 3',5'-Di-O-benzoyl-2'-O-methyluridine crystallized from methanol to give 3.4 g (75 %), white crystals, mp 132°–134° C. (lit., C. Chavis, et.al., J. Org. Chem., 1982, 47, 202, mp 132°–133° C.). The filtrate was chromatographed on silica gel (30 g) with hexanes-ethyl acetate to give 0.5 g (11%) additional crystalline product. $^1$H NMR (DMSO-d$_6$): δ3.36 (s, 3H, OCH$_3$), 4.42 (m, 1H, H-2'), 4.5–4.7 (m, 3H, H-4',5'), 5.60 (m, 1H, H-3'), 5.64 (d, J=8 Hz, 1H, H-5), 5.92 (d, J=3 Hz, 1H, H-1'), 7.5–8.1 (m, 11H, Bz-H, H-6), 11.45 (s, 1H, NH).

EXAMPLE 6

2'-O-Methyluridine.

A sample of 3', 5'-di-O-benzoyl-2'-O-methyl-uridine (0.80 g, 17 mmoles) was deprotected in a mixture of methanol (65 ml) and concentrated ammonium hydroxide (35 ml) overnight at room temperature. The solution was allowed to evaporate to an oil in the fume hood. The residue was triturated with ether (100 ml). The resulting solid was rinsed with ether and dried to afford 0.38 g (86%) of 2'-O-methyluridine as a white solid, mp 158°–159° C. (lit. C. Chavis, ibid., mp 156°–159° C.). (DMSO-d$_6$): δ3.34 (s, 3H, OCH$_3$), 3.5–3.7 (m, 2H, H-5'), 3.7–3.9 (m, 2H, H-3',4'), 4.14 (m, 1H, H-2'), 5.19 (m, 2H, 3',5'—OH), 5.66 (d, J=8 Hz, 1H, H-5), 5.87 (d, J=5 Hz, 1H, H-1'), 7.95 (d, J=8 Hz, 1H, H-6), 11.35 (br s, 1H, N—H). Anal. calcd for C$_{10}$H$_{14}$N$_2$O$_6$ (258.23): C, 46.51; H, 5.46; N, 10.85. Found: C, 46.57; H, 5.49; N, 10.82.

EXAMPLE 7

3',5'-Di-O-benzoyl-2'-O-methyl-5-methyluridine.

Thymine (8.0 g, 63 mmoles) was glycosylated as described in the General Method of Example 2. The crude dibenzoyl product containing a β/α ratio of 16:1 (αH-1'at 6.41 ppm) was chromatographed on silica gel (600 g) using a gradient of ethyl acetate in hexanes (40–60%) to give 23.2 g of foam which contained 3.5% of the α anomer. The pure β product crystallized from methanol to give 16.1 g (55%) of first crop of 3',5'-di-O-benzoyl-2'-O-methyl-5-methyluridine as white crystals, mp 128°–130° C. Subsequent crops were contaminated with the α anomer. $^1$H NMR (DMSO-d$_6$): δ1.68 (s, 3H, 5-CH$_3$), 3.34 (s, 3H, OCH$_3$), 4.41 (m, 1H, H-2'), 4.5–4.7 (m, 3H, H-4',5'), 5.67 (m, 1H, H-3'), 5.98 (d, J=5 Hz, 1H, H-1'), 7.5–8.1 (m, 11H, Bz-H, H-6), 11.49 (s, 1H, NH). Anal. Calcd for C$_{25}$H$_{24}$N$_2$O$_8$ (480.46): C, 62.49; H, 5.04; N, 5.83. Found: C, 62.49; H, 4.92; N, 5.75.

EXAMPLE 8

2'-O-Methyl-5-methyluridine.

3,5-Di-O-benzoyl-2'-O-methyl-5-methyluridine (14.3 g, 30 mmoles) was dissolved in methanol (130 ml) and concentrated ammonium hydroxide (65 ml) for 24 hours. The solvent was evaporated under reduced pressure and the residue was triturated with ether to give 6.5 g (80%) of white solid. An analytical sample was crystallized from absolute ethanol to afford 2'-O-methyl-5-methyluridine as white needles, mp 192°–193° C. (lit., E. Ootsuka, H. Inoue, Japanese Patent 89-85456, 4 Apr. 1989, mp 197°–198° C.). $^1$H NMR (DMSO-d$_6$): δ1.79 (s, 3H, 5-CH$_3$), 3.35 (s, 3H, OCH$_3$), 3.5–3.7 (m, 2H, H-5'), 3.7–3.9(m, 2H, H-3',4'), 4.15 (m, 1H, H-2'), 5.17 (m, 2H, 3',5'—OH), 5.87 (d, J=5 Hz, 1H, H-1'), 7.80 (s, 1H, H-6), 11.37 (br s, 1H, N—H). Anal. Calcd for C$_{11}$H$_{16}$N$_2$O$_6$ (272.26): C, 48.52; H, 5.92; N, 10.29. Found: C, 48.56; H, 5.88; N, 10.22.

EXAMPLE 9

3',5'-Di-O-benzoyl-2'-O-methyl-5-fluorouridine

5-Fluorouracil (4.1 g, 32 mmoles) was glycosylated as described in the General Method of Example 2 to give 15.1 g of crude dibenzoyl product containing a β/α ratio of 15:1 (α, H-1' at 6.41 ppm). The pure β product crystallized from methanol in two crops for a total of 10.4 g (68%) of 3',5'-Di-O-benzoyl-2'-O-methyl-5-fluorouridine as white needles, mp 182°–184° C. $^1$H NMR (DMSO-d$_6$): δ3.35 (s, 3H, OCH$_3$), 4.44 (m, 1H, H-2'), 4.5–4.7 (m, 3H, H-4',5'), 5.60 (m, 1H, H-3'), 5.93 (d, J=4 Hz, 1H, H-1'), 7.5–8.0 (m, 10H, Bz-H), 8.06 (d, J=7 Hz, 1H, H-6), 12.02 (s, 1H, NH).

EXAMPLE 10

2'-O-Methyl-5-fluorouridine.

3',5'-Di-O-benzoyl-2'-O-methyl-5-fluorouridine (9.6 g, 20 mmoles) was dissolved in methanol (350 ml) which had been previously saturated with ammonia at −20° C. The solution was sealed in a stainless steel bomb at room temperature for 17 hours and then concentrated to an oil under reduced pressure. The oil was chromatographed on silica gel (200 g) using ethyl acetate to give 5.4 g (98%) of 2'-O-methyl-5-fluorouridine as a white solid. A portion (0.5 g) was crystallized from ethyl acetate/toluene to yield 0.4 g of white needles as the analytical sample, mp 151°–152° C. (lit. M. J. Robins, et. al., J. Am. Chem. Soc., 89, 7381 (1976)., mp 144°–147° C.). $^1$H NMR (DMSO-d$_6$): δ 3.39 (s, 3H, OCH$_3$), 3.5–3.7 (m, 2H, H-5'), 3.7–3.9 (m, 2H, H-3',4'), 4.13 (m, 1H, H-2'), 5.18 (d, J=6 Hz, 1H, 3'—OH), 5.35 (br t, 1H, 5'—OH), 5.81 (dd, 1H, H-1'), 8.35 (d, J=7 Hz, 1H, H-6), 11.40 (br d, 1H, N—H). Anal. Calcd for C$_{10}$H$_{13}$N$_2$O$_6$ (276.22): C, 43.48; H, 4.74; N, 10.14. Found: C, 43.56; H, 4.63; N, 10.02.

EXAMPLE 11

3',5'-Di-O-benzoyl-2'-O-methyl-5-nitrouridine.

5-Nitrouracil (5.5 g, 35 mmoles) was glycosylated as described in the General Method of Example 2 to give 17.9 g of crude product containing a β/α ratio of 9:1 (α, H-1'at 6.46 ppm). The pure β product crystallized from methanol to afford 10.0 g (56%) of 3',5'-di-O-benzoyl-2'-O-methyl-5-nitrouridine as white needles, mp 187°–189° C. Further concentration of the mother liquor gave only inseparable, contaminated product. $^1$H NMR (DMSO-d$_6$): δ3.41 (s, 3H, OCH$_3$), 4.5–4.8 (m, 4H, H-2',4',5'), 5.62 (m, 1H, H-3'), 5.97 (d, J=3 Hz, 1H, H-1'), 7.5–8.1 (m, 10H, Bz-H), 9.16 (s, 1H, H-6), 12.23 (br s, 1H, NH).

EXAMPLE 12

2'-O-Methyl-5-nitrouridine.

A sample of the dibenzoyl intermediate 3',5'-di-O-benzoyl-2'-O-methyl-5-nitrouridine (2.0 g, 4 mmoles) was dissolved in methanol (50 ml). Sodium metal (0.1 g, 4 mmoles) was added and the solution was stirred at room temperature for 17 hours. The sodium salt of 2'-O-methyl-5-nitrouridine precipitated. The solid was triturated with ether (50 ml) and dried under reduced pressure at 100° C. overnight to 11 g (88%) of white powder, mp 237° C. (dec. with eff.). A portion was neutralized by dissolving into 10% aqueous methanol and passing through an Amberlite IRC-50 weak acid resin column. The solution was concentrated and dried under reduced pressure to 2'-O-methyl-5-nitrouridine as a tan paste. $^1$H NMR (DMSO-d$_6$): δ3.47 (s, 3H, OCH$_3$), 3.5–3.7 (m, 1H, H-5'), 3.7–3.9 (m, 3H, H- 3',4',5') 4.15 (1H, H-2'), 5.17 (d J=7 Hz, 1H, 3'—OH), 5.44 (br t, 1H, 5'—OH), 5.79 (br s, 1H, H-1'), 9.72 (s, 1H, H-6), 12.05 (br s, 1H, N—H). Attempts to crystallize out an analytical sample of the neutral product failed due to the unstable nature of 3',5' -di-O-benzoyl-2'-O-methyl-5-nitrouridine. The crude sodium salt of 2'-O-methyl-5-nitrouridine analyzed as follows; Anal. Calcd for $C_{10}H_{12}N_3NaO_8$ (325.22): C, 36.93; H, 3.72; N, 12.92. Found: C, 36.57; H, 3.71; N, 12.44.

EXAMPLE 13

4-Chloro-1-(2-O-methyl-3,5-di-O-benzoyl-β-D-ribofuranosyl)-2 (1H)-pyrimidinone.

To prepare 4-chloro-2-trimethylsilylethoxy-pyrimidine, a solution of trimethylsilylethanol (10.0 g, 85 mmoles) in anhydrous tetrahydrofuran was cooled to −68° C. in an isopropanol dry ice bath and then treated with n-butyllithium (33.8 ml of a 2.5M solution) dropwise over 30 minutes. This mixture was warmed to −25° C. and then added via cannula to a solution of 2,4-dichloropyrimidine (12.6 g, 85 mmoles) at −68° C. while maintaining anhydrous conditions. After addition, the mixture was allowed to warm to room temperature over 30 minutes and stirred at this temperature for 1 hour. The clear yellow solution was diluted with diethyl ether (200 ml) and then washed with cold water and cold, saturated sodium bicarbonate solution. The organic layer was dried over magnesium sulfate and evaporated to yield a thick amber oil. This oil was kept under vacuum overnight and then flash chromatographed over a silica gel column (7.5×8.5 cm) using chloroform as eluent. The solvent was thoroughly evaporated and the resulting yellowish oil was crystallized at −68° C. from a minimum volume of hexane to give 20.3 g (91%) of silylated base as white waxy plates. $^1$H NMR (DMSO-$d_6$): δ0.10 (s, 9H, SiCH$_3$), 1.08 (t, 2H, SiCH$_2$), 4.40 (t, 2H, OCH$_2$), 7.27 (d, 1H, H-5), 8.55 (d, $J_{6,5}$=4.5 Hz, 1H, H-6).

A portion of the 4-chloro-2-trimethylsilylethoxy-pyrimidine (6.0 g, 26 mmoles) was glycosylated as described in the General Method of Example 2 to give 12.1 g (96%) of crude dibenzoyl product containing a β/α ratio of 14:1 (α, H-1'at 6.39 ppm). Due to its reactivity, the product was used as is for further derivatization. $^1$H NMR (deuteriochloroform): δ 3.64 (s, 3H, OCH$_3$), 4.33 (m, 1H, H-2'), 4.6–4.9(m, 3H, H-4',5',5''), 5.20 (m, 1H, H-3'), 6.03 (br s, 1H, H-1'), 6.15 (d, $J_{6,5}$=5.8 Hz, 1H, H-6), 7.4–8.2 (m, 11H, aromatic and H-5).

EXAMPLE 14

1-N-(N-Carbamoyl-2-nitro-ε-propenamid-3-yl-amino-2-O-methyl-β-D-ribofuranose.

The title compound was produced as follows: Dibenzoyl intermediate 3',5'-di-O-benzoyl-2'-O-methyl-5-nitrouridine from Example 11 (16.0 g, 31 mmoles) was dissolved in methanol (350 ml) previously saturated with ammonia at −20° C. The solution was sealed in a stainless steel bomb for 17 hours at room temperature. The solvent was removed under reduced pressure. The product precipitated from methanol to give 7.9 g (80%), white solid, mp 182°–183° C. (dec.); $^1$H NMR (DMSO-$d_6$): δ3.41 (s, 3H, OCH$_3$), 3.45 (br s, 2H, H-5',5'), 3.59 (m, 1H, H-4'), 3.76 (m, 1H, H-3'), 4.09 (m, 1H, H-2'), 4.88 (t, J=5 Hz, 1H, 5'—OH), 4.99 (d, J=6 Hz, 1H, 3'—OH), 5.42 (dd, J=6 Hz and J=9 Hz, 1H, H-1'), 8.35(br s, 1H, H-2), 8.83 (d, J=9 Hz, 1H, 1-NH), 10.00 (br s, 2H, NH$_2$), 10.55 (br s, 1H, 5-NH). Upon deuterium oxide exchange, H-1' collapses to a doublet (J=6 Hz) and the H-2 singlet sharpens. Anal. Calcd for $C_{10}H_{16}N_4O_8$ (320.27): C, 37.50; H, 5.04; N, 17.50. Found: C, 37.48; H, 5.03; N, 17.31.

EXAMPLE 15

3',5'-Di-O-benzoyl-2'-O-methyl-5-iodouridine

5-Iodouracil is glycosylated as described in the General Method of Example 2 to give the title compound.

EXAMPLE 16

3',5'-Di-O-benzoyl-2'-O-methyl-5-(1-propynyl)uridine.

3',5'-Di-O-benzoyl-2'-O-methyl-5-iodouridine is treated with (Ph$_3$P)$_2$PdCl$_2$ and CuI in Et$_3$N as per the procedure of, Eric De Clercq, E,. et. al., *J. Med. Chem.* 1983, 26, 661–666), to give the title compound.

EXAMPLE 17

2'-O-Methyl-5-(1-propynyl)uridine.

3',5'-Di-O-benzoyl-2'-O-methyl-5-(1-propynyl)uridineis treated as in Example 3 to give, after purification, the title compound.

EXAMPLE 18

2-Thio-1-(3,5-di-O-benzoyl-2-O-methyl-β-D-ribofuranosyl)-pyrimidin-4-one.

2-Thiouracil (1.282 g, 10 mmol), a few crystals of ammonium sulfate, a few drops of TMSCl and HMDS (20 ml) were refluxed overnight. The clear, greenish solution was evaporated under the exclusion of moisture. A solution of 2-O-methyl-1,3,5-tri-O-benzoyl-βD-ribose (4.76 g, 10 mmol) in acetonitrile (50 ml) was added to give a clear solution. SnCl$_4$ is added and the mixture became turbid and then immediately became clear thereafter. The mixture was stirred for three hours and then poured into a stirred mixture of sat'd NaHCO$_3$ and CH$_2$Cl$_2$(200/400 ml). The organic layer was separated, dried over Na$_2$SO$_4$, filtered and evaporated. The amorphous residue was crystallized from hot EtOH to yield the title compound as colorless needles (1.895 g, 39%). $^1$H NMR (CDCl$_3$): δ10.3 (s, 1H, NH), 7.8 (d, 1H, H6), 6.7 (s, 1H, H'1), 5.7 (d, 1H, H5), 3.6 (s, 3H, OCH$_3$).

EXAMPLE 19

2-Thio-S-(aceton-1-yl)-1-(3,5-di-O-benzoyl-2-O-methyl-μ-D-ribofuranosyl)pyrimidin-4-one.

Chloroacetone (0.35 ml, 4.35 mmol) was added to a solution of 2-thio-1-(3',5'-di-O-benzoyl-2'-O-methyl-μ-D-ribofuranosyl)pyrimidin4-one in CH$_2$Cl$_2$ (920 ml) and triethylamine (0.81 ml, 5.8 mmol). After 16, hrs water was added and the organic layer washed with water, dried with Na$_2$SO$_4$, filtered and evaporated to yield the product as a tlc homogeneous material. $^1$H NMR (CDCl$_3$): δ7.5 (d, 1H, H6), 6.0 (s, 1H, H1), 5.8 (d, 1H, H5), 4.05 (s, 1H, CH$_2$), 3.4 (s, 3H, OCH$_3$), 2.3 (s, 3H, COCH$_3$).

EXAMPLE 20

2-(Aceton-1-yl)-1-(3,5-di-O-benzoyl-2-O-methyl-β-D-ribofuranosyl)pyrimidin-4-one.

Crude2-thio-S-(aceton-1-yl)-1-(3',5'-di-O-benzoyl-2'-O-methyl-β-D-riboduranosyl)pyrimidin- 4-one was dissolved in toluene (20 ml) and triphenylphosphine and KOtBu (0.29 ml of a 1N solution in THF, Aldrich) was added. The mixture was stirred at 125° C. overnight. The solvent was evaporated and the residue was purified by flash column chromatography (5 cm; chloroform/EtOAc, 2:1) to give the product as a slightly yellowish foam (1.26 g, 80% from starting 2-thiouracil). $^1$H NMR (CDCl$_3$): δ13.9 (b m, 1H, N·H··O), 7.25 (s, 3H, CH$_3$), 4.98 (s, 1H, CH), 3.5 (s, 3H, OCH$_3$), 2.2 (s, 1H, COCH$_3$).

EXAMPLE 21

4-Chloro-2-trimethylsilylethoxy-pyrimidine.

A solution of trimethylsilylethanol (10 g, 85 mmol) in 30 ml anhydrous THF was cooled to −68° C. in a dry ice/isopropanol bath. A solution of n-butyl lithium (33.8 ml, 2.5M in THF) was added dropwise over 15 min. The solution was stirred for 10 min at this temperature and then added to a solution of 2,4- dichloropyrimidine (12.62 g. 85 mmol) in 75 ml THF at −35° C. to −25° C. The final yellowish solution was allowed to come to room temperature under an argon atmosphere then stirred at this temperature for 1 hr. This solution was diluted with 200 mL of Et$_2$O and washed with cold water (100 ml), sat'd NaHCO$_3$ (100 ml) and brine, then dried over MgSO$_4$, filtered and evaporated to yield a tan syrup. This syrup is crystallized from hexanes at −60° C. to yield the title compound as a light yellow solid, 17.8 g (91%). $^1$H NMR (CDCl$_3$): δ8.36 (d, 1H, H-6), 6.93 (d, 1H, 5-H), 4.43 and 1.17 (t,t; 4H; CH$_2$CH$_2$), 1.06 (bs, 9H. TMS).

EXAMPLE 22

4-Chloro-1-(2-O-methyl-3,5-di-O-benzoyl-β-D-ribofuranosyl)-pyrimidin-2-one.

4-Chloro-2-trimethylsilylethoxy-pyrimidine (3.5 g, 15.2 mmole) and 2-O-methyl-1,3,5-tri-O-benzoyl-α-D-ribose (7.0 g, 15.2 mmole) were dissolved in acetonitrile (100 ml). This solution was treated with trimethylsilyl trifluoromethanesulfonate (2.8 g, 15.2 mmole) and stirred for 1.5 hours. The reaction mixture was concentrated to an oil and redissolved in 300 ml CH$_2$Cl$_2$. The CH$_2$Cl$_2$ solution was washed with cold concentrated sodium bicarbonate, dried over magnesium sulfate, filtered, and evaporated to an oil. The oil was coevaporated with acetonitrile and dried to a brown foam to give 6.70 g (91%) crude product.

EXAMPLE 23

4-(1-Hexyn-1-yl)-1-(2-O-methyl-3,5,-di-O-benzoyl-β-D-ribofuranosyl)pyrimidin-2-one.

Bis-triphenylphosphine palladium (II) dichloride (422 mg, 4.3 mmole) and copper (I) iodide (114 mg, 4.3 mmole) were suspended in anhydrous THF (100 ml) and degassed with argon for 10 min. The orange suspension was treated with triethylamine (5 ml) and 1-hexyne (2.96 g, 41 mmole) and stirred for 5 min. A solution of 4-chloro-1-(2-O-methyl-3,5,-di-O-benzoyl-β-D-ribofuranosyl)pyrimidin-2-one (6.74 g, 13.9 mmole) in THF (25 ml) was added all at once. The reaction mixture was stirred for 2 hours at room temperature and evaporated to an oil. The residue was purified by silica gel column chromatography. Elution with chloroform (500 ml) and then chloroform/acetone (98:2, 2l), pooling of appropriate fractions and evaporation gave a yield of 3.84 g (52.7%).

EXAMPLE 24

4-(2-Hydroxy-1-hexen-1-yl)-1-(2-O-methyl-3,5,-di-O-benzoyl-β-D-ribofuranosyl)pyrimidin-2 -one.

4-(1-Hexyn-1-yl)-1-(2-O-methyl-3,5,-di-O-benzoyl-β-D-ribofuranosyl)pyrimidin-2-one was dissolved in acetone (40 ml) and to this solution was added mercuric sulfate dissolved in H$_2$O (10 ml) and acetic acid (10 ml). This solution was stirred at room temperature for 5 hours. The reaction was purified by silica gel column chromatography. Pooling of appropriate fractions and concentration gave 225 mg (19%) of the title compound.

EXAMPLE 5

4-(2,5-Dihydroxy-1-hexen-1-yl)-1-(2-O-methyl-2,5-di-O-benzoyl-β-D-ribofuranosyl)pyrimidine- 2-one.

Bis-triphenylphosphine palladium (II) dichloride (3.18 g, 0.45 mmole) and copper (I) iodide (0.85 g, 4.5 mmole) were suspended in anhydrous THF (100 ml) and degassed with argon for 10 min. The orange suspension was treated with triethylamine (5 ml) and 4-pentyn-1-ol (2.27 g, 27 mmole) and stirred for 5 min. A solution of 4-chloro-1-(2-O-methyl-3,5,-di-O-benzoyl-β-D-ribofuranosyl)pyrimidin-2-one (4.8 g, 19.9 mmole) in THF (25 ml) was added all at once. The reaction mixture was stirred for 2 hours at room temperature and evaporated to an oil. The residue was purified by silica gel column chromatography. Elution with ethyl acetate:hexanes (50:50, 500 ml; 90:10 1000 ml) pooling of appropriate fractions and evaporation gave a yield of 1.87 g (33%).

EXAMPLE 26

6-Methyl-3,5-bis(trimethylsiloxy)-1,2,4-triazine.

A mixture of 6-azathymine (purchased from Aldrich Chemical Co.) (5.0 g, 39.4 mmol), hexamethyldisilazane (HMDS) (15 ml), and chlorotrimethylsilane (TMSCl) (0.5 ml), in a round bottom flask (50 ml) fitted with a condenser and a drying tube, is refluxed by heating in an oil bath (150° C.); NH$_4$Cl collects as white powder in the condenser. When a clear solution was obtained (1 hr.), the excess of HMDS/TMSCl was removed by distillation at 30° C./torr (bath temp 100° C.). The residual oil crystallized on drying under vacuum (0.1 torr), giving 6.57 g (61%) of 6-methyl-3,5-bis(trimethylsiloxy)-1,2,4-triazine, mp 43° C.

EXAMPLE 27

2-(2-O-Methyl-3,5-di-O-benzoyl-β-D-ribofuranosyl)-6-methyl- 1,2,4-triazine-3,5(2H,4H)-dione.

6-Methyl-3,5-bis(trimethylsiloxy)-1,2,4-triazine is treated as in the general Method of Example 2 to yield the title compound.

EXAMPLE 28

2'-O-Methyl-6-azathymidine, i.e., [2-(2-O-methyl-β-D-ribofuranosyl)-6 -methyl-1,2,4-triazine-3-5(2H,4H)-dione].

2-(2-O-Methyl-3,5-di-O-benzoyl-β-D-ribofuranosyl)-6-methyl-1,2,4-triazine-3-5 (2H,4H)-dione is treated as per example 3 to yield the title compound.

EXAMPLE 29

N-4-Benzoyl-2'--O-methyl-5-methylcytidine.

A solution of 2'-O-methyl-5-methyluridine (15.3 g, 32 mmoles) in dry pyridine (350 ml) was stirred at 3°–5° C. under an atmosphere of argon. Phosphorous oxychloride (6.8 ml, 73 mmoles) was added dropwise over 1 hour. After stirring for an additional 1 hour, a solution of 1,2,4-triazole (15.3 g, 221 mmoles) in dry pyridine (100 ml) was added in one portion. The reaction was allowed to warm to room temperature and to stir for 24 hours. The reaction was diluted with CH$_2$Cl$_2$ (500 ml) and washed with water (4×400 ml). The organic layer was dried (magnesium sulfate) and concentrated under reduced pressure to a foam. In a separate flask, benzamide (34 g, 281 mmoles) and sodium hydride (60% in oil, 10.4 g, 260 mmoles) were suspended in dioxane (350 ml) and heated to 65° C. for 1 hour. The resulting solution was cooled to room temperature and added to the nucleoside. The mixture was stirred for 2 hours, then treated with methanol (175 ml) to cleave the benzoyl esters. After 5 hours, the reaction was neutralized with glacial acetic acid (14.7 ml). The solvent was removed under reduced pressure. The residue was extracted with ether to separate the product from solid by-products. The ether layer was filtered and concentrated under reduced pressure. The residue was chromatographed on silica gel (300 g) using ethyl acetate-hexanes (4:1). The product N-4-benzoyl-2'-O-methyl-5-methylcytidine (ca 4 g, 33% crude yield) was slightly contaminated with benzamide and was used as such for further derivatization. An analytical sample (0.25 g) crystallized from ethyl acetate as white needles, mp 222°–224° C. $^1$H NMR (DMSO-d$_6$): δ2.03 (s, 3H, 5-CH$_3$), 3.42 (s, 3H, OCH$_3$), 3.5–4.0 (m, 4H, H-3',4',5'), 4.17 (m, 1H, H-2'), 5.20 (d, J=6 Hz, 1H, 3'—OH), 5.32 (br t, 1H, 5'—OH), 5.89 (d, J=4 Hz, 1H, H-1), 7.5–7.6 (m, 3H, m and p Bz-H), 9.72 (s, 1H, H-6), 8.21 (m, 3H, o Bz-H and H-6), 12.95 (br s, 1H, N—H). Anal. Calcd for C$_{18}$H$_{21}$N$_3$O$_6$ (375.38): C, 57.58; H, 5.64; N, 11.20. Found: C, 57.61; H, 5.63; N, 11.15.

EXAMPLE 30

N-4-Benzoyl-5'-O-(4,4'-dimethoxytrityl)-2'-O-methyl-5-methylcytidine.

To a solution of N-4-Benzoyl-2'-O-methyl-5-methylcytidine (4.5 mmol) in dry pyridine (40 ml) is added 4,4'-dimethoxytrityl chloride (4.5 mmol). The reaction mixture is stirred at room temperature for three hours and evaporated. The residue is purified by silica gel column chromatography. Elution with an appropriate organic solvent, pooling of appropriate fractions, and evaporation will give the title compound.

EXAMPLE 31

N-4-Benzoyl-5'-O-(4,4'-dimethoxytrityl)-3'-O-[(N,N-diisopropylamino)-2-cyanoethoxyphosphite]-2'-O-methyl-5-methylcytidine.

To a solution of N-4-benzoyl-5'-O-(4,4'-dimethoxytrityl)-2'-O-methyl-5-methylcytidine (13 mmol) and diisopropylethylamine (5.5 ml) in THF (50 ml) is added chloro-β-cyanoethoxy-N,N-diisopropylaminophosphine (14 mmol). The mixture is stirred at room temperature for 2 hours. The mixture is filtered and the filtrate is purified by silica gel column chromatography. Elution with an appropriate organic solvent, pooling of appropriate fractions and evaporation will give the title compound.

EXAMPLE 32

DMT/Phosphoramidite

Further derivatazation of 2'-O-methyl-α-D-ribofuranose compounds to their DMT/phosphoramidites is accomplished using standard methods as illustrated in Examples 30 and 31. In preparing monomeric compounds, protection of exocyclic functional groups with base labile protecting groups is effected. The resulting compound is tritylated with 4,4'-dimethoxytrityl chloride, and phosphitylated with chloro-β-cyanoethoxy-N,N-diisopropylaminophosphine to give the desired monomeric compound.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A process for the large scale production of diazomethane, diazopropane or diazoethane comprising:
   a. generating diazomethane or diazoethane through contact of a nitroso precursor compound with an aqueous base in the presence of an organic solvent for diazomethane or diazoethane;
   b. drying the solution of organic solvent and said diazomethane or diazoethane a plurality of times with a basic drying agent compatible with diazomethane or diazoethane and said solvent;
   c. storing said dry solution of diazomethane or diazoethane in said solvent in a storage vessel;
   d. while maintaining a dry, chemically inert gaseous environment in the vessels for drying and storage; and
   e. delivering said organic solvent containing the diazomethane or diazoethane from said storage vessel to a reaction vessel while maintaining said inert gaseous environment.

2. The process of claim 1 wherein said solvent has a density greater than the aqueous base.

3. The process of claim 1 wherein said solution of said diazomethane or diazoethane is maintained at about 0° C. to about 15° C.

4. The process of claim 1 wherein said drying and said storing steps of said organic solvent containing said diazomethane or diazoethane is effected in separate vessels and organic solvent containing said diazomethane or diazoethane is transferred between said separate vessels using a differential in pressure.

* * * * *

UNITED STATES PATENT AND TRADEMARK OFFICE
CERTIFICATE OF CORRECTION

PATENT NO. : 5,459,243         Page 1 of 2
DATED      : October 17, 1995
INVENTOR(S): Oscar Acevedo, Bruce Ross, Robert S. Andrews, Robert Springer and Phillip D. Cook It is certified that error appears in the above-indentified patent and that said Letters Patent is hereby corrected as shown below:

Column 1, line 12, change "-α-ribose" to -- -α-D-ribose--.
Column 1, line 38, change "oligonucleotides" to --oligoribonucleotides--.
Column 1, line 57, change "2'-methyl" to --2'-O-methyl--.
Column 2, line 9, change "2'-O-methyl-" to --2-O-methyl- --.
Column 2, line 10, change "1,3,5 tri-O-benzoyl-e-D-ribose" to --1,3,5-tri-O-benzoyl-α-D-ribose--.
Column 2, line 14, change "st. al." to --et. al.--.
Column 2, line 22, change "methyl-1,3,5-O" to --methyl-1,3,5-tri-O".
Column 7, line 2, change "1-(3,5-di-O-Benzoyl-2 methyl" to --1-(3,5-di-O-benzoyl-2-O-methyl--.
Column 8, line 12, change "1H" to --$^1$H--.
Column 8, line 34, change "1H-1'" to --1H, H-1'--.
Column 8, line 50, change "(sharp, CN)" to --(sharp, -CN)--.
Column 8, line 53, change "H1'" to --H-1'--.
Column 8, line 64, change "H-1')" to --H-1'--.
Column 9, line 19, before "(DMSO-$d_6$)" insert --$^1$H NMR--.
Column 10, line 27, change "$C_{10}H_{13}N_2O_6$" to --$C_{10}H_{13}FN_2O_6$--.
Column 10, line 61, change "4.15 (1H," to --4.15 (m, 1H,--.
Column 10, line 62, change "(dJ=7" to --(d, J=7--.
Column 12, line 18, change "-tri-O-benzoyl-βD-ribose" to -- -tri-O-benzoyl-α-D-ribose--.
Column 12, line 34, change "(s, 1H, H'1)" to --(s, 1H, H1')--.
Column 12, line 38, change "-methyl-μ-" to -- -methyl-β- --.
Column 12, line 41, change "-methyl-μ-" to --methyl-β- --.
Column 12, line 42, change "bofuranosyl)pyrimidin4-one" to --bofuranosyl)pyrimidin-4-one--.
Column 12, line 47, change "(s, 1H, H1) to --(s, 1H, H1')--.

UNITED STATES PATENT AND TRADEMARK OFFICE
CERTIFICATE OF CORRECTION

PATENT NO. : 5,459,243

DATED : October 17, 1995

INVENTOR(S) : Oscar Acevedo, Bruce Ross, Robert S. Andrews, Robert Springer and Phillip D. Cook It is certified that error appears in the above-indentified patent and that said Letters Patent is hereby corrected as shown below:

Column 13, line 64, change the heading "EXAMPLE 5" TO --EXAMPLE 25--.
Column 15, line 9, change "H-1)" to --H-1)"--.
Column 16, claim 1, line 15, after "diazomethane" insert --diazopropane--.

Signed and Sealed this

Twentieth Day of February, 1996

BRUCE LEHMAN

Attest:

Attesting Officer

Commissioner of Patents and Trademarks